(12) United States Patent
Latham

(10) Patent No.: US 8,455,619 B2
(45) Date of Patent: Jun. 4, 2013

(54) POLYPEPTIDE SYNTHESIS FOR DRUG DELIVERY

(76) Inventor: Keith R. Latham, Abingdon, VA (US)

( * ) Notice: Subject to any disclaimer, the term of this patent is extended or adjusted under 35 U.S.C. 154(b) by 417 days.

(21) Appl. No.: 12/623,584

(22) Filed: Nov. 23, 2009

(65) Prior Publication Data

US 2010/0130723 A1    May 27, 2010

Related U.S. Application Data

(60) Provisional application No. 61/117,748, filed on Nov. 25, 2008.

(51) Int. Cl.
*C07K 2/00* (2006.01)
(52) U.S. Cl.
USPC .......................................... 530/333; 530/342
(58) Field of Classification Search
USPC ................................... 530/333, 342
See application file for complete search history.

(56) References Cited

U.S. PATENT DOCUMENTS

| | | | |
|---|---|---|---|
| 5,767,227 A | 6/1998 | Latham et al. | |
| 6,077,930 A | 6/2000 | Nobori et al. | |
| 6,413,550 B1 | 7/2002 | Milstein et al. | |
| 6,656,458 B1 | 12/2003 | Philippe et al. | |
| 7,018,654 B2 | 3/2006 | Kirk et al. | |
| 7,060,708 B2 | 6/2006 | Piccariello et al. | |
| 7,163,918 B2 | 1/2007 | Piccariello et al. | |
| 7,316,815 B2 | 1/2008 | Philippe et al. | |
| 2002/0099013 A1 | 7/2002 | Piccariello et al. | |
| 2005/0119445 A1 | 6/2005 | Geller et al. | |
| 2007/0232529 A1 | 10/2007 | Mickle et al. | |
| 2008/0021192 A1 | 1/2008 | Iyer et al. | |

OTHER PUBLICATIONS

Duran (ACS Symposium Series (2008), 977 (Polymers for Biomedical Applications), 371-390).*
Kovacs (J. Polymer Science: Part A-1, vol. 4, 1553-1562, 1966).*
Wieringa (Macromolecules 29(8), 3032-4, 1996).*
International Search Report (ISR) and Written Opinion for PCT/US09/65477.
Theodora W. Greene and Peter G.M. Wuts, Protective Groups in Organic Synthesis, 1991, John Wiley & Sons, Inc., US.
H. Block, Poly(γ-Benzyl-L-Glutamate) and Other Glutamic Acid Containing Polymers, 1983, Gordon and Breach, Science Publishers, Inc., New York, NY.

* cited by examiner

*Primary Examiner* — David Lukton
(74) *Attorney, Agent, or Firm* — Stockwell & Smedley, PSC

(57) ABSTRACT

The present invention provides improved methods for the synthesis of polypeptide or peptide-linked compounds via a NCA-based polymerization reaction that produces high product yields in much less time. Such improved methods are achieved by application of a higher temperature and/or reduced pressure to the reaction such that an NCA-containing monomer melts.

25 Claims, No Drawings

POLYPEPTIDE SYNTHESIS FOR DRUG DELIVERY

CROSS-REFERENCE TO RELATED APPLICATIONS

This application claims the benefit of priority from U.S. Provisional Application No. 61/117,748, filed Nov. 25, 2008. The entire contents and disclosures of the above applications are hereby incorporated by reference.

FIELD OF THE INVENTION

The present invention relates to improved methods for synthesizing polypeptides or peptide-linked compounds based on techniques utilizing N-carboxyanhydride (NCA) amino acids and/or compounds.

BACKGROUND

A number of methods and products have been developed to provide sustained release of active agents or drugs for their safe and effective administration to humans or animals. For example, sustained release of an active agent may allow a reduction in the daily dosing requirement and a more even and long-term absorption into the body of an individual. Enteric coatings on tablets, microencapsulation of active agents into microspheres, liposomes, etc., as well as the use of macromolecules, such as polypeptides, polysaccharides, etc., have been described previously. Direct covalent attachment of active agents to polypeptides as a way of providing sustained release has also been proposed. However, existing methods for synthesizing peptide-conjugated active agents are limited by their impractical reaction schemes that are generally not suitable for large-scale industrial, agricultural, or pharmaceutical applications. Therefore, a need exists in the art for improved methods of polypeptide or polymer synthesis having improved yield and efficiency that are further capable of incorporating active agents into a growing polypeptide chain.

SUMMARY

According to a first aspect of the present invention, a method is provided comprising the following steps: (a) combining one or more initiators and one or more NCA-containing monomers in a reaction vessel to form a reaction mixture; and (b) heating the reaction mixture to an elevated temperature at or above the melting point of at least one of the NCA-containing monomers, such that at least one of the NCA-containing monomers melts at the elevated temperature.

According to a second broad aspect of the present invention, a method is provided comprising the following steps: (a) combining one or more initiators, one or more NCA-containing monomers, and an aprotic solvent in a reaction vessel to form a reaction mixture; and (b) heating the reaction mixture to an elevated temperature at or above the melting point of at least one of the NCA-containing monomers, such that at least one of the NCA-containing monomers melts at the elevated temperature.

According to a third broad aspect of the present invention, a method is provided comprising the following steps: (a) combining one or more initiators and one or more NCA-containing monomers in a reaction vessel to form a reaction mixture; (b) heating the reaction mixture to an elevated temperature at or above the melting point of at least one of the NCA-containing monomers, such that at least one of the NCA-containing monomers melts at the elevated temperature; and (c) applying a reduced pressure to the reaction mixture.

DETAILED DESCRIPTION OF THE PREFERRED EMBODIMENTS

Definitions

Where the definition of terms departs from the commonly used meaning of the term, applicant intends to utilize the definitions provided below, unless specifically indicated.

For purposes of the present invention, the term "NCA" refers to N-carboxyanhydride.

For purposes of the present invention, the terms "aprotic solvent" refers to a solvent that does not exchange (i.e., neither accepts nor donates) protons with a molecule dissolved in the solvent.

For purposes of the present invention, the term "phosgene compound" may include any compound that is structurally related to phosgene. For example, a phosgene compound may include phosgene, diphosgene, triphosgene, etc.

For purposes of the present invention, the term "initiating group" refers to a chemical group or substituent of a molecule, compound, or polymer, such as an initiator and/or a growing polymer or polypeptide of a NCA-based polymerization reaction, that is capable of initiating an NCA-based polymerization reaction. An initiating group may include an amino group, hydroxyl group, sulfhydryl group, etc.

For purposes of the present invention, the term "initiator" refers to any molecule, compound, polymer, peptide, etc., which is capable of initiating an NCA-based polymerization reaction and which includes an initiating group(s).

For purposes of the present invention, the term "NCA-containing monomer" refers to a monomer that has been chemically converted to include an NCA moiety (or moieties), such as by reaction with a phosgene compound. Such NCA-containing monomer may be incorporated as a monomer into a polymer synthesized during a NCA-based polymerization reaction. Such NCA-containing monomer may include an NCA-compound and/or an NCA-amino acid.

For purposes of the present invention, the term "monomer" refers to an organic compound or amino acid which may be chemically converted to include an NCA moiety (or moieties), such as by reaction with a phosgene compound. Such a monomer may include any compound structurally related to an amino acid that contains an amino group and a carboxyl group bonded to the α-carbon of such monomer to be capable of forming the NCA moiety. Such a monomer may include any compound that is capable of forming an NCA moiety. For example, such a monomer may include any of the naturally occurring L-amino acids, D-amino acids, and other modified amino acids and amino acid derivatives.

For purposes of the present invention, the term "base monomer" in reference to a particular NCA-containing monomer refers to a monomer used to make, or converted to become, the NCA-containing monomer.

For purposes of the present invention, the term "NCA-compound" refers to an organic compound which has been chemically converted to include an NCA moiety (or moieties), for example, by reaction with a phosgene compound. In general, such an organic compound chemically converted to become an NCA-compound should be structurally related to an amino acid and contain an amino group and a carboxyl group on the α-carbon atom of the organic compound to be able to form the NCA moiety. For example, such NCA-compound may refer to any active agent or drug that is structurally related to and/or derived from an amino acid, such that the organic compound is capable of being chemically converted to include the NCA moiety. For example, such an NCA-compound may include an NCA-amino acid.

For purposes of the present invention, the term "NCA-amino acid" refers to an amino acid which has been chemically converted to include an NCA moiety, for example, by reaction of the amino acid with a phosgene compound.

For purposes of the present invention, the term "α-carbon" in reference to an organic compound or amino acid refers to a carbon atom of the compound or amino acid that is bonded to four chemical substituents or groups including an amino or ammonium group (e.g., $NH_2$ or $NH_3^+$), a carboxyl group (e.g., COOH or $COO^-$), and a side chain (R), such that the amino and carboxyl groups are able to form peptide bonds with other organic compounds and/or amino acids. An α-carboxyl group of an organic compound or amino acid is a carboxyl group covalently bonded to an α-carbon, and an α-amino group of an organic compound or amino acid is a amino group covalently bonded to an α-carbon.

For purposes of the present invention, the term "side chain" in reference to an organic compound or amino acid refers to one of four chemical substituents on the α-carbon atom of the organic compound or amino acid that may be allowed to vary.

For purposes of the present invention, the term "NCA moiety" refers to an N-carboxyanhydride ring structure involving the carboxyl group and the amino group of the α-carbon atom of a monomer, which may be formed by reaction of the monomer with a phosgene compound. Such NCA moiety is opened upon reaction with an initiating group to form a peptide bond with expulsion of carbon dioxide ($CO_2$) as a by-product.

For purposes of the present invention, the term "NCA-based" in reference to a reaction generally refers to a reaction based on the formation or utilization of an NCA-containing monomer. Such an NCA-based reaction may include an NCA-based polymerization reaction.

For purposes of the present invention, the terms "NCA-based polymerization reaction" or "NCA-based polymerization" refer interchangeably to the synthesis of a polymer via an NCA-based method. Such a reaction may result from combining one or more NCA-containing monomer(s) and at least one initiator(s) into a single reaction mixture. NCA-based polymerizations involve a ring opening of the NCA moiety by reaction with an initiating group to form a peptide bond with the expulsion of $CO_2$ as a by-product.

For purposes of the present invention, the term "reaction mixture" generally refers to the reactants (e.g., NCA-containing monomer(s), initiator(s), etc.) and the resulting reaction products (e.g., polymer products) of a reaction (e.g., a polymerization reaction) as well as any solvent that may be present or contained within a single reaction vessel.

For purposes of the present invention, the term "polymer" refers to a product synthesized by a NCA-based polymerization reaction. Such polymers may include any length of polymer, including dimers, trimers, oligomers, etc. Each polymer formed by a NCA-based polymerization reaction may comprise any combination of an initiator and one or more types of monomer(s) linked together by peptide bonds.

For purposes of the present invention, the term "homopolymer" refers to a polymer product of a polymerization reaction comprising identical initiator and monomer units.

For purposes of the present invention, the term "peptide-linked compound" refers to a polymer product of an NCA-based polymerization reaction comprising a non-amino acid compound linked to one or more monomers by peptide bond(s). Such non-amino acid compounds may include drugs or active agents.

For purposes of the present invention, the term "polypeptide" refers to a polymer product of a polymerization reaction comprising two or amino acids linked by peptide bonds.

For purposes of the present invention, the terms "active agent" or "drug" refer interchangeably to compounds having a biological or pharmaceutical activity or effect that may be used as an initiator or chemically converted to become an NCA-containing monomer for an NCA-based polymerization reaction.

For the purposes of the present invention, the term "reaction vessel" refers to any vessel, such as a container, flask, tube, bottle, beaker, etc., which may be used to contain or hold a reaction mixture.

For the purposes of the present invention, the term "boiling point" refers to the temperature at which the liquid phase of a substance or solvent, such as an aprotic solvent, has a vapor pressure equal to or slightly greater than the pressure of the surrounding environment. Generally speaking, a substance or solvent transitions from a liquid phase to a gaseous or vapor phase at or above the boiling point for the substance or solvent. The boiling point for a substance or solvent is dependent on the surrounding pressure (or partial pressure of the substance or solvent) and may change when the pressure or partial pressure surrounding such substance or solvent is reduced.

For the purposes of the present invention, the terms "boil" or "boils" refer to the process of a substance or solvent, such as an aprotic solvent, transitioning from a liquid phase to a gaseous or vapor phase at, near, or above the boiling point for such substance or solvent.

For the purposes of the present invention, the term "melting point" refers to the temperature at which the solid phase of a substance, such as an NCA-containing monomer(s), is at or near equilibrium with the liquid phase of such substance at a given pressure. Generally speaking, a substance, such as an NCA-containing monomer(s), transitions from a solid phase to a liquid phase at or above the melting point for the substance.

For the purposes of the present invention, the terms "melt" or "melts" refer to the process of a substance, such as an NCA-containing monomer(s), transitioning from a solid phase to a liquid phase at, near, or above the melting point for such substance. A substance, such as an NCA-containing monomer(s), may be allowed to melt at, near, or above the melting point for the substance if such substance is not dissolved in a solution.

Description

The use of "carrier" polypeptides incorporating pharmaceutically active agents to provide sustained release and improved shelf-life has been described previously. See, e.g., U.S. Pat. No. 5,767,227 (Latham et al.), issued Jun. 16, 1998, the contents and disclosure of which are hereby incorporated by reference. For example, a pharmaceutically active agent may be complexed with a separate polypeptide as a macro-formulation defined as the blending of an active agent with synthetic polypeptides in bulk. Alternatively, a pharmaceutically active agent may be complexed with a polypeptide as a micro-formulation defined as the incorporation of an active agent into the tertiary structure (e.g., a hydrophobic pocket) of a polypeptide. Methods based on the use of polypeptides with active agents are generally aimed at sequestering the active agent from being absorbed into the bloodstream or from exerting its targeted activity until, for example, the matrix of polypeptides is sufficiently digested by enzymes and/or by chemical hydrolysis to release the active agent.

However, macro- and micro-formulations of active agents and polypeptides may have a number of drawbacks. For example, truly uniform distribution of the active agent in the polypeptide carrier may be difficult to achieve, and different active agent molecules may be complexed with individual polypeptide molecules of the carrier matrix in a heterogeneous manner. As a result, formulations may have an uneven distribution of the active agent in the polypeptide carrier, an unreliable degree of protection of the active agent from degradation or premature release, and/or variability in the release and pharmacokinetics of the active agent upon administration to an individual. These issues may be particularly problematic when administering compounds having potent biological activity.

To ensure greater uniformity in the manner in which active agents are incorporated into polypeptide-containing compositions, active agents or drugs may instead be directly or covalently linked to polypeptides or polymers. By covalently attaching active agents or drugs to polypeptide molecules or polymers, greater consistency in sustained release properties and prolonged shelf-life may be achieved. With oral administration of peptide-linked drugs, such synthetic "pro-drug" polypeptides or polymers may pass through the gastro-intestinal tract until sufficient proteolysis has occurred to either liberate the drug or reduce the length of the peptide-linked drug to dimers, trimers, oligomers, etc., which are sufficiently small to cross the intestinal epithelium and enter the bloodstream. In addition, peptide-linked drugs of small to moderate size may cross the intestinal epithelium and enter the bloodstream through active mechanisms. In general, drugs which are covalently linked to polypeptides may be pharmacologically inert due to their sequestration in the gut as well as their inability to bind target receptors. Similar steric or size constraints may also have the effect of limiting access of drugs to the brain until the peptide-linked drug is reduced sufficiently in size or shortened by digestion to allow the drug to cross the blood-brain barrier.

Covalent attachment of polypeptides or polymers to drugs may have other pharmaceutical or agricultural benefits. For example, covalent attachment of polypeptides or polymers to drugs may serve to protect these drugs from chemical degradation in the gut or while circulating in the bloodstream by enveloping the drug within its folded structure until proteolytic digestion exposes and releases the drug from the polymer. Such protective function may also have the effect of increasing the shelf-life of the drug when purified or formulated into various pharmaceutical compositions. Depending on the specific linkage and position of the drug in the polymer, steric hindrances may also serve to lower the affinity of the drug for a particular receptor or a sub-class of binding sites until complete digestion of polymer is achieved to release the drug. Such final "activation" or release of the drug may occur at sites of action to allow for greater targeting of its effect in peripheral tissues, thus providing a "pro-pro-drug" approach that combines properties of sustained release and targeted activity. Steric protection provided by the polymer or peptide linkage to a drug may also serve to protect the drug from modification and clearance before it has had the opportunity to exert its biological effect. For example, a peptide-linked amphetamine compound may be resistant to monoamine oxidase degradation. Yet another benefit of covalent attachment of polypeptides or polymers may be improved solubility of certain drugs in aqueous environments.

A number of techniques for synthesizing polypeptide or peptide-linked molecules in vitro have been described. For example, stepwise blocking/de-blocking methods have been known in the art for many years as a way of building polypeptide molecules. However, these methods generally require multiple chemical steps for the addition of each amino acid to the polymer resulting in a time-consuming process with a low product yield.

An alternative, solution-based approach to synthesizing a peptide molecule may be achieved using a carbodiimide method. This approach generally relies on the use of a carbodiimide molecule (e.g., dicyclohexylcarbodiimide (DCC), etc.) to activate a carboxyl (e.g., —COOH) group of one compound, such as an amino acid, to produce a highly reactive intermediate which may then react and bond to other compounds or molecules, such as through an amino group of an amino acid to form a peptide bond. This method may be used to link two amino acids together or to couple an amino acid (or preformed peptide) to an active agent. However, this carbodiimide reaction scheme is not capable of self-polymerization and merely provides a coupling or linking mechanism for joining two molecules. Once a carbodiimide-activated molecule, such as a carbodiimide-activated amino acid, is allowed to react with another compound, the reaction is complete. To synthesize a polypeptide containing, for example, three or more amino acids using the carbodiimide method, a stepwise approach would be necessary to carry out repeated rounds of activation and coupling. Such a step-wise approach is a time-consuming process having a substantial reduction in yield to carry out these multiple reaction steps. Furthermore, any additional side groups which might react with a carbodiimide-activated intermediate may need to be blocked to avoid formation of unintended and undesired by-products. In addition, carbodiimides tend to form racemic mixtures of amino acids which may be incorporated into peptide-linked molecules or polymers. Considering that most naturally occurring amino acids are L-amino acids, racemization may make enzyme digestion of carbodiimide-produced polypeptides difficult or impossible, and a large proportion of active agents incorporated into carbodiimide-produced polypeptides or amino acid conjugates may be rendered inaccessible or biologically inactive. Although the addition of triazolol compounds (e.g., hydroxybenzotriazole (HOBt), etc.) have reduced this racemic effect, carbodiimide-based methods remain a less practical approach for synthesizing polypeptide molecules.

One effective method for synthesizing polypeptides or peptide-linked polymers that overcomes issues of racemization and non-spontaneous polymerization is the Fuchs-Farthing approach of generating highly reactive N-carboxyanhydride (NCA) intermediates of compounds or amino acids. Unlike the carbodiimide approach discussed above, this NCA-based method preserves the stereoisomeric state of compounds or amino acids incorporated into a growing polypeptide or polymer chain, i.e., such NCA-based methods are stereospecific. Thus, products formed by this method will have normal peptide bonds which may be recognized and hydrolyzed by, for example, proteases, as well as other natural enzymes.

In general, NCA-based methods for synthesizing polymers, such as polypeptides, peptide-linked compounds, etc., may involve two basic reactions: (1) formation of one or more NCA-containing monomer(s) from one or more types of monomer(s), and (2) polymerization of these monomer(s) to form a desired polymer product(s) upon introduction of at least one type of initiator. In the first reaction, NCA-containing monomer(s), which may include NCA-compounds and NCA-amino acids, may be formed by reacting one or more monomer(s) with a phosgene compound in an aprotic solvent to form a temporary N-chlorocarbonyl intermediate, which then cyclizes to form an NCA moiety of the NCA-containing monomer(s) with release of two HCl molecules (See, e.g., Example 1).

NCA-containing monomer(s) synthesized during the first reaction step may then be used in an NCA-based polymerization reaction to form a polymer, such as a polypeptide, peptide-linked compound, etc., which is initiated by the introduction of an initiator. Because both the amino group and carboxyl group on the α-carbon of a monomer form part of the cyclized ring structure of the NCA moiety of an NCA-containing monomer, the α-amino group of an NCA-containing monomer is not available to function as an initiating group until the NCA ring structure (i.e., NCA moiety) of the NCA-containing monomer is opened to reform the α-amino group of its base monomer. Therefore, the NCA-based polymerization reaction may not begin until an initiator is introduced to open the NCA-ring structure (or NCA moiety) by forming a peptide bond between the α-carbonyl group of the NCA-containing monomer and the initiating group of an initiator, with the release of carbon dioxide ($CO_2$) as a by-product. As a result of opening the ring structure of the NCA moiety of an NCA-containing monomer during an NCA-based polymerization reaction, the α-amino group of the base monomer of the NCA-containing monomer is reformed and able to function as an "initiating group" for another NCA-containing monomer (i.e., for the next round of polymerization). Through this iterative process within a reaction mixture, the NCA-based polymerization reaction may occur spontaneously, and a polymer, such as a polypeptide, peptide-linked compound, etc., may be formed. Such NCA-based polymerization reaction may occur through either protic or aprotic mechanisms. See, e.g., Block, H., "Poly(Gamma-Benzyl-L-Glutamate) and other Glutamic Acid Containing Polymers," Vol. 9., Ed. M. B. Huglin, (Gordon and Breach Science Publishers, New York, 1983), the entire contents and disclosure of which is hereby incorporated by reference.

Therefore, another major advantage of NCA-based approaches, compared to the other "step-wise" blocking/deblocking or carbodiimide methods, is that a desired polymer, such as a polypeptide, peptide-linked compound, etc., may be synthesized spontaneously in a single reaction mixture without the need for intervening purification steps and/or repeated addition of new reactants or solvents. After one or more initiator(s) are provided to initiate an NCA-based polymerization reaction, NCA-containing monomers, which are generally soluble in aprotic solvents, react to form a polymer, such as a polypeptide, peptide-linked compound, etc., which may then precipitate because these polymer products are generally insoluble in aprotic solvents. Accordingly, this conversion in solubility of NCA-containing monomers upon incorporation of their base monomer into a polymer product of an NCA-based polymerization reaction may be used as a basis for further washing and purification of these polymerized products from other reaction components.

Despite the promise of using NCA-based methods to synthesize polymers, such as polypeptides, peptide-linked compounds, etc., for a variety of agricultural, pharmaceutical, or industrial applications, the practicality of these methods has been limited by variable yields and long reaction times. According to many conventional approaches to using NCA-based methods, NCA-containing monomers and an initiator are generally placed in a reaction mixture containing an aprotic solvent, and the reaction mixture is allowed to proceed for many hours or even days (e.g., from about 18 to about 90 hours) at or near room temperature (e.g., about 25° C.). See, e.g., U.S. Pat. No. 7,018,654 (Kirk et al.), issued Mar. 28, 2006; U.S. Pat. No. 7,060,708 (Piccariello et al.), issued Jun. 13, 2006; U.S. Pat. No. 7,163,918 (Piccariello et al.), issued Jan. 16, 2007; and U.S. Pub. Pat. Appl. No. 2002/0099013 (Piccariello et al.), published Jul. 25, 2002, the entire contents and disclosures of which are hereby incorporated by reference. In addition to long reaction times, yields may be quite variable. Due to these long reaction times, undesired contaminants and side products may commonly form, which may become predominant in the reaction mixture. Largely for these reasons, large-scale industrial and pharmaceutical applications of NCA-based approaches to synthesize polypeptides or other polymer products have been limited.

Improvements in NCA-based methods for the synthesis of polymers, such as polypeptides, peptide-linked compounds, etc., are provided herein. According to embodiments of the present invention, an alternative NCA-based method is proposed wherein the polymerization reaction step is carried out at an elevated temperature and/or reduced pressure. As a result of this new approach, the polymerization reaction proceeds at a much more rapid rate to produce higher product yields in much less time. In contrast to most previously described NCA-based methods requiring many hours or days to prepare polypeptide or polymer products, embodiments of the present invention generally require only minutes to complete with high yields of polymer products of desired length, composition, etc. The improvements achieved by embodiments of present methods over many prior attempts relying on NCA-based methods may serve to enable the practical application of NCA-based methods in a broad range of industrial, agricultural, and pharmaceutical contexts.

According to embodiments of the present invention, one or more NCA-containing monomer(s) may be combined with one or more initiator(s) to form a reaction mixture in a reaction vessel. An aprotic solvent may also be used initially to facilitate homogeneous mixing of NCA-containing monomer(s) and initiator(s). However, in contrast to prior methods, the NCA-based polymerization reaction according to embodiments of the present invention is warmed (e.g., slowly or gradually warmed) well above room temperature and maintained at an elevated temperature at or above the melting temperature of the one or more NCA-containing monomer(s) included in the reaction mixture, such that the polymerization reaction proceeds with molten NCA-containing monomer(s) functioning like a "solvent" for the reaction mixture. According to embodiments of the present invention, such an elevated temperature is also at or above the boiling point for the aprotic solvent to cause most or all of the aprotic solvent originally present in the reaction mixture to evaporate. For example, depending on the exact combination of NCA-containing monomer(s) and initiator(s) as well as the type of aprotic solvent used, the NCA-based polymerization reaction according to some embodiments may be carried out or maintained at a temperature within a range of from about 50° C. to about 75° C. Alternatively, for example, the NCA-based polymerization reaction may be carried out or maintained at a temperature within a range of from about 55° C. to about 70° C.

According to some embodiments, the elevated temperature may depend on the degree to which the pressure is reduced. For example, the boiling point for the aprotic solvent may be lower when the pressure applied to the polymerization reaction is reduced below normal atmospheric pressure. Different conditions or combinations of elevated temperature and/or reduced pressure may be used as a way to achieve (i) melting of one or more NCA-containing monomer(s), and/or (ii) evaporation of the aprotic solvent. According to some embodiments, such an elevated temperature may be at or near a temperature where rapid evolution of $CO_2$ as a by-product of the reaction becomes visible at a given pressure. For example, the reaction may be monitored and held at a temperature where evolution of $CO_2$ is rapid but sufficiently under control.

According to embodiments of the present invention, the selection of elevated temperature for the NCA-based polymerization reaction may be important and should balance different considerations. For example, the NCA-based polymerization reaction should be warm enough to allow the reaction to proceed at a rapid rate, such that the process is useful. However, the NCA-based polymerization reaction may generally not be heated above certain temperatures (e.g., above about 75° C.) because NCA-containing monomer(s), such as NCA-amino acid(s) and/or NCA-compound(s), may degrade or revert back to their base monomer(s), and unintended or undesired products may be created at these temperatures. Therefore, according to embodiments of the present invention, an acceptable temperature for the NCA-based polymerization reaction may be anywhere within a range of about 50° C. to about 75° C. depending on the circumstances. It may also be important that the reaction be brought to the elevated temperature in a gradual and/or asymptotic fashion (e.g., in a heated water bath at the desired temperature) to ensure that the reaction mixture is not overheated, even temporarily, as this may cause degradation or reversion of NCA-containing monomers or the formation of undesirable products as described above.

Many previous attempts at using NCA-based methods to synthesize polypeptides or other polymers have generally been performed at lower temperatures (e.g., room temperature) and not at elevated temperatures. There are several reasons why NCA-based polymerization reactions may not have been performed at these higher temperatures. Many aprotic solvents are volatile and may thus evaporate at the higher temperatures described herein. However, these aprotic solvents may have been considered necessary, or at least desirable, to ensure adequate solubility and mixing of reaction components, such as initiators and monomers, over the course of a polymerization reaction to form desired products of the reaction. In contrast to these previous or conventional approaches, it has been found that an NCA-based polymerization reaction according to embodiments of the present methods relying on elevated temperature and/or reduced pressure may be used to reliably synthesize desired polymer products with high yield, fewer contaminants, and shorter reaction times.

Increasing the temperature of an NCA-based reaction may have also raised concerns about degradation of NCA-containing monomer(s), reversion of NCA-containing monomer(s) back to their base monomer(s), or the formation of undesired by-products as mentioned above. In contrast to conventional approaches, however, NCA-based polymerization methods according to embodiments of the present invention have been shown to proceed at a faster rate under such conditions without degradation or reversion of NCA-containing monomer(s). Other concerns about raising the temperature of an NCA-based polymerization reaction may have been based on the perception that the polymerization reaction may become too exothermic, thus making the temperature of the reaction difficult to control. There may have also been a concern that evaporation of solvent at higher temperatures may cause the reaction product to become too dense to recover easily in solution. In contrast to previous or conventional approaches, however, products synthesized according to embodiments of the present invention are generally quite pure and easily recoverable in solution, thus allowing products synthesized by the present invention to be easily formulated with other substances into compositions, such as pharmaceutical compositions, for patient therapy (See, e.g., Example 4).

According to embodiments of the present invention, an NCA-based polymerization reaction may also be carried out under reduced pressure. Not only may the reduced pressure work in tandem with the elevated temperature to encourage evaporation of the aprotic solvent, such reduced pressure may further increase the rate of synthesis of reaction products (i.e., the rate of polymerization). By conducting the reaction under a reduced pressure or vacuum, $CO_2$ generated as a product of the polymerization reaction may be removed from the reaction. Without being bound by any theory, any $CO_2$ present in the reaction mixture or environment may slow formation of the polymer product or possibly drive the reaction in a reverse direction according to principles of chemical equilibrium. Accordingly, by reducing or minimizing the concentration of $CO_2$ in the reaction environment, the polymerization reaction may be allowed to proceed more rapidly, and more polymer products, such as polypeptides, peptide-linked compounds, etc., may be synthesized over a given period of time.

According to some embodiments, the polymerization reaction may be carried out at a reduced pressure that is sufficient to continuously remove $CO_2$ produced by the reaction. At a minimum, such reduced pressure may be sufficiently less than the surrounding pressure of the environment to at least cause a measurable or significant flow of gas away from the reaction. Such reduced pressure may be much lower or only slightly reduced relative to the surrounding atmospheric pressure. For example, such reduced pressure may be anywhere from a little over (i.e., slightly above) zero inches of Hg to about 20 inches of Hg (i.e., a pressure reduced by about 10 inches of Hg to about 20 inches of Hg assuming a pressure in the surrounding environment of about 30 inches of Hg). However, the reduced pressure may theoretically be at any level sufficiently less than the pressure of the surrounding environment to continuously and/or significantly remove the $CO_2$ produced by the NCA-based polymerization reaction.

By elevating the temperature and reducing the pressure of an NCA-based polymerization reaction as described herein, large amounts of relatively pure polymer product may be formed in a short period of time. For example, when the NCA-based polymerization reaction is allowed to proceed at an elevated temperature and reduced pressure, high yields of desired polymer products have been achieved in as little as about 15 minutes. Indeed, a more rapid rate of product synthesis has been observed with both elevated temperature and reduced pressure compared to an NCA-based polymerization reaction carried out at either elevated temperatures or reduced pressures alone.

According to some embodiments, the NCA-based polymerization reaction may be carried out a temperature that is at or above the boiling point for an aprotic solvent depending on the pressure applied to the reaction. An aprotic solvent may be used initially to promote homogeneous mixing of NCA-containing monomer(s) and initiator(s) in a reaction mixture before the temperature is raised. Evaporation of aprotic solvent may be necessary to ensure that the NCA-containing monomer(s) are no longer in solution and allowed to melt and become a "solvent" for the NCA-based polymerization reaction. Therefore, the choice of aprotic solvent in relation to the NCA-containing monomer(s) may be important, such that the aprotic solvent evaporates or boils at or below the melting temperature for the NCA-containing monomer(s). Such aprotic solvent chosen for the reaction may also need to have a boiling point below temperatures at which NCA-containing monomer(s) become unstable or revert back to their base monomer(s) if reaction the temperature is above the melting temperature for the NCA-containing monomer(s).

Boiling points for various aprotic solvents under standard conditions that may be used in conjunction with method embodiments of the present invention are generally known in the art. Aprotic solvents that may be used may include, for example, perfluorohexane, pentane, hexane, cyclohexane, carbon tetrachloride, benzene, carbon disulfide, diisopropyl ether, diethyl ether, t-butyl methyl ether (MTBE), chloroform, ethyl acetate, tetrahydrofuran (THF), methylene chloride, 2-butanone (MEK), acetone, acetonitrile, dichloromethane, nitrobenzene, etc. Although some aprotic solvents may have boiling points above the preferred range of temperatures, such aprotic solvents may still be used under reduced pressure conditions (i.e., such solvents may evaporate at lower temperatures under reduced pressure). Under conditions where the pressure is reduced only slightly to sufficiently draw off the $CO_2$ produced by the reaction, boiling points for aprotic solvents may only be slightly altered from their known values under standard conditions.

One known group has described the performance of an NCA-based reaction at a temperature above room temperature. See, e.g., U.S. Pat. No. 6,656,458 (Phillipe et al.), issued Dec. 2, 2003 and U.S. Pat. No. 7,316,815 (Phillipe et al.), issued Jan. 8, 2008. However, each of the example reactions provided are carried out in an aprotic solvent having a high boiling point (e.g., toluene with a known boiling point of about 111° C. under standard conditions). Thus, these descriptions only provide reaction temperatures that are below the boiling point for the aprotic solvent used. As a result, melting of reaction components, such as NCA-containing monomer(s), would not occur since the reaction remains in solution. Furthermore, neither of these two descriptions make any mention of carrying out a polymerization reaction at a reduced pressure. Therefore, in contrast to prior methods, embodiments of the present invention provide an NCA-based polymerization reaction carried out at an elevated temperature and/or reduced pressure, such that aprotic solvent that may be present in the reaction mixture evaporates and/or NCA-containing monomer(s) are allowed to melt and function as a "solvent" for the NCA-based polymerization reaction mixture.

According to some embodiments, while the temperature of the NCA-based polymerization reaction containing initiator(s) and NCA-containing monomer(s) is slowly increased to an elevated temperature, any aprotic solvent that may have been initially used may evaporate, and evolution or frothing of $CO_2$ as a by-product of the reaction may become visible. Once the rate of evolution of $CO_2$ is no longer visible or becomes relatively slowed, the reaction may be considered complete or nearly complete. Other visible evidence may be used to indicate that the reaction has reached or is close to completion. For example, over the course of an NCA-based polymerization reaction, the reaction mixture may transition from being a homogeneous mixture in the beginning to becoming increasingly viscous or thick. Finally, a relatively pure precipitate or powder of reaction product, which may appear white, may be formed when the aprotic solvent initially present in the reaction mixture is mostly or fully evaporated and product is formed. Completion (or near completion) of the polymerization reaction may also be monitored or verified by an infrared (IR) spectrometric approach measuring absorbance of reaction components present in the reaction mixture. For example, an NCA-containing monomer(s) typically may absorb light at two IR wavelengths (e.g., having wavenumbers of about $1780\pm5$ cm$^{-1}$ and $1855\pm5$ cm$^{-1}$), thus providing a characteristic absorption pattern that is different than other amino acid derivatives. However, once most or all of the NCA-containing monomer(s) have been incorporated into polymer products, the NCA moiety and its characteristic absorption pattern may be lost or diminished. Therefore, the polymerization reaction may be considered complete or nearly complete when absorption at these wavelengths is substantially reduced, minimized, or no longer observed.

Although further purification steps may be necessary, the polymer products, such as polypeptides, peptide-linked compounds, etc., synthesized by embodiments of the present invention may be pure or relatively pure. Often times, very little of the NCA-containing monomer(s) and initiator(s) may remain unreacted after the reaction has reached or neared completion. In addition, very little, if any, $CO_2$ or leftover solvent may remain after the reaction nears completion because the reaction is carried out at a higher temperature and/or reduced pressure. According to some embodiments, a solid precipitate or powder of the polymer product may be mostly all that is left of the reaction mixture once the reaction has reached or neared completion, which may then be subjected to further purification. During an NCA-based polymerization reaction, the NCA-containing monomer(s), which are generally soluble in aprotic solvents, may react to form a polymer product, such as a polypeptide, a peptide-linked compound, etc., which may no longer be soluble in aprotic solvents. Therefore, a polymer product of an NCA-based polymerization reaction will generally form a solid precipitate or polymer, which may be purified on this basis using aprotic solvents to wash away any lingering impurities and reaction components, such as solvent, unreacted NCA-containing monomer(s) or initiator(s), etc. For pharmaceutical applications, purified products of an NCA-based polymerization reaction may be suitable for direct formulation into compositions designed for oral or parenteral administration.

An NCA-based polymerization reaction method according to embodiments of the present invention for synthesizing polymers, such as polypeptides, peptide-linked compounds, etc., may be extremely versatile, thus allowing for a wide variety of products to be made. By adjusting (i) the ratio of an initiator to NCA-containing monomer(s), (ii) the one or more type(s) of initiator(s), and (iii) the one or more type(s) of NCA-containing monomer(s), polymers synthesized by embodiments of present methods may vary greatly.

According to embodiments of the present invention, an initiator used in an NCA-based polymerization reaction may potentially include conventional amines, such as triethylamine, diethylamine, hexylamine, etc. However, initiators may potentially include any compound having an initiating group, such as an amino group, a hydroxyl group, a sulfhydryl group, etc. Initiators that may be used with embodiments of the present invention may include any appropriate active agent, drug, or compound having an initiating group, such as, for example, amphetamine, serotonin, catecholamines, such as L-DOPA or dopamine, 3,5,3',5'-tetraiodothyronine (thyroxine or T4), 3,5,3'-triiodo-L-thyronine (triiodothyronine or T3), any natural or unnatural L- or D-amino acid, any modified L- or D-amino acid, etc., or even water. Although only one type of initiator may be required in a given NCA-based polymerization reaction, more than one initiator may be used according to some embodiments to synthesize a mixture of different polymer products in a single NCA-based polymerization reaction mixture. According to some embodiments where an amino acid is used as an initiator, the "free acid" forms of such amino acids may be used as opposed to the HCl or Na salts which may be less effective as initiators under some circumstances.

According to some embodiments, because an initiator becomes covalently attached to the growing polypeptide or peptide-linked compound synthesized during an NCA-based polymerization reaction, an amino acid or an appropriate active agent or drug may be used as an initiator to avoid incorporation of heterologous initiators, such as triethylamine, diethylamine, hexylamine, etc., which may not provide any useful benefit and may actually be harmful and/or complicate regulatory approval for pharmaceutical products. According to some embodiments, although an initiator molecule may often be different than the base monomer(s) of the one or more types of NCA-containing monomer(s) used in an NCA-based polymerization reaction, the initiator may alternatively be the same as the base monomer of the one or more types of NCA-containing monomer(s). For example, a polymer of glutamic acid may be synthesized by using glutamic acid as an initiator and NCA-glutamic acid as an NCA-containing monomer (See, e.g., Example 2). Such a polyglutamic acid polymer may be useful, for example, as an excipient in tablet formulations to control specific dissolution properties and drug release (See, e.g., Example 4).

According to embodiments of the present invention, an NCA-containing monomer used in an NCA-based polymerization reaction may be any NCA-compound or NCA-amino acid, which may be made by converting its base monomer into an NCA-containing monomer having an NCA moiety. An NCA-amino acid may include an L-amino acid, D-amino acid, modified amino acid, or derivatives thereof. An NCA-compound used as an NCA-containing monomer in an NCA-based polymerization reaction may be made from a base monomer that is not an amino acid. However, an NCA-compound used as an NCA-containing monomer must have both an amino group or ammonium group (e.g., $NH_2$ or $NH_3^+$) and a carboxyl group (e.g., COOH or $COO^-$) on the α-carbon of the base monomer similarly to amino acids to allow the formation of the necessary NCA-ring structure or NCA moiety of the NCA-compound. For example, a number of drugs, hormones, or other bioactive compounds may be derived from amino acids and thus retain both the α-amino and α-carboxyl groups needed to form an NCA moiety. Therefore, according to embodiments of the present invention, any compound that may be converted into an NCA-compound that is able to form peptide bonds in an NCA-based polymerization reaction may be used as the base monomer of an NCA-compound. The base monomer of the NCA-compound may then be incorporated into the growing polymer product, such as a polypeptide, peptide-linked compound, etc., formed during an NCA-based polymerization reaction. Such monomers may include, for example, NCA-compound(s) made or converted from L-DOPA; thyroid hormones including 3,5,3',5'-tetraiodothyronine (thyroxine or T4) and 3,5,3'-triiodo-L-thyronine (triiodothyronine or T3); etc.

According to embodiments of the present invention, regardless of whether an NCA-containing monomer used in an NCA-based polymerization reaction is an NCA-amino acid or an NCA-compound, such NCA-containing monomer must generally be able to ultimately form two peptide bonds: (1) a first peptide bond formed between the α-carboxyl group of the base monomer of an NCA-containing monomer and an α-amino group of a monomer covalently attached to one end of a growing polymer product (or to an initiator) with the α-amino group of the growing polymer product or initiator acting as an initiating group; and (2) a second peptide bond formed between the α-amino group of the base monomer of the NCA-compound (covalently attached to the growing polymer as a result of the first peptide bond) and the next monomer added to the chain. By opening the ring structure of the NCA moiety of an NCA-containing monomer during formation of the first peptide bond, the α-amino group of the base monomer covalently attached to the growing polymer product is reformed and free to be used as an initiating group for the next round of monomer addition to the growing polymer product of the NCA-based polymerization reaction. Otherwise, if the NCA-compound was not able to participate in ultimately forming both peptide bonds, the NCA-based polymerization reaction would terminate prematurely.

Some amino acids, such as glutamine or asparagine, may not be suitable for use as monomers because of the difficulty in converting them into NCA-amino acids. However, according to some embodiments, these amino acids may still be used as initiators. For example, a glutamine-initiated polypeptide having a "tail" of glutamic acid monomers may be used as an effective glutamine source, such as for tissue culture or nutriceutical applications. Delayed release of glutamine may overcome its short half-life with some applications.

Other issues may affect the way other amino acid monomers are used. For example, some amino acids may have functional groups on their side chains that may interfere with the formation or stability of the NCA-amino acid and/or their use in an NCA-based polymerization reaction. For example, many of the same chemical groups that may be used as initiating groups (e.g., amino, hydroxyl, sulfhydryl, etc.) present on side chains of monomers may react with other NCA-containing monomers or function as an "initiator" resulting in the production of undesirable products. Therefore, many side groups present on amino acids or other monomer compounds may need to be blocked prior to their use in the polymerization reaction as NCA-containing monomers to avoid these effects. Suitable blocking groups that may be used for different chemical groups according to some embodiments of the present invention (as well as methods for their use) are known in the art. See, e.g., Greene, T. W. and Wuts, T. G. M. "Protective groups in organic synthesis," $2^{nd}$ Edition, John Wiley & Sons (New York, 1991), the contents and disclosure of which are hereby incorporated by reference. For example, according to some embodiments, the amine group on the side chain of lysine may need to be blocked (e.g., by acetylation) to allow use of NCA-lysine in a polymerization reaction (See, e.g., Examples 6-8 showing blocking and deblocking of Lysine-NCA for polymerization with T3). However, unlike poly-lysine containing polymers, a poly-glutamic acid containing polymer may be synthesized according to embodiments of the present invention with reasonably high product yield (e.g., 69%; see Example 1) without needing to block the acidic side chains. In contrast, previous NCA-based methods for synthesizing poly-glutamic acid relied on additional blocking and de-blocking steps to achieve reasonable yield.

According to some embodiments, an active agent or drug compound may be incorporated as an initiator into a polymer or peptide-linked compound product of an NCA-based polymerization reaction with an attached "tail" of one or more types of amino acids. Such amino acids used may be chosen on the basis of the chemical environment that the peptide-linked compound or polymer is likely to encounter. For example, amphetamine, which may be used as a CNS stimulant to induce wakefulness or to treat ADHD, may be linked as an initiator to a polymer or peptide-linked compound with a tail of glutamic acids for oral administration (See, e.g., Example 3). Alternatively, 3,5,3',5'-tetraiodothyronine (T4) or 3,5,3'-triiodothyronine (T3) may be linked as an initiator to a polymer or peptide-linked compound with a tail of glutamic acids for oral administration. By using amino acid monomers having acidic side chains to build the tail portion of the polymer product of an NCA-based polymerization reaction, the polymer may assume a more folded tertiary structure in the environment of the stomach where the pH is low because carboxyl groups are fully protonated. However, as the polymer travels through the digestive tract, the pH gradually increases and more of the side chain carboxyl groups of the polymer become ionized, thus causing the polymer to assume a more extended conformation that is more accessible to protease digestion. This property may be used to encourage more sustained or delayed release of the drug.

An opposite pattern of release may be achieved according to some embodiments with amino acids, such as lysine, having basic side chains. Unlike acidic side chains, side chains containing basic groups, such as amino groups, may be positively charged in low pH and thus fully extended and vulnerable to proteolytic digestion. For example, either amphetamine or 3,5,3',5'-tetraiodothyronine (T4) or 3,5,3'-triiodothyronine (T3) may be linked as an initiator to a polymer or peptide-linked compound with a tail of lysines, such as for oral administration. (See, e.g., Examples 6-8 showing an example of blocking and deblocking of Lysine-NCA for polymerization with T3 as an initiator, which may be similarly applied to synthesis of polymers with amphetamine as an initiator). Different pH considerations may be relevant to designing peptide-linked drugs or polymers administered in different ways, such as by injection into blood or tissue or other routes of administration. For example, peptide-linked drugs or polymers with intrinsic buffering capacity (e.g., glutamic acid containing peptide-linked drugs or polymers) may be preferred for parenteral administration. Another example according to some embodiments is synthesis of poly-lysine polymers for use in cell culture or wound healing applications. According to these embodiments, lysine may be used as an initiator with blocked Lysine-NCA for NCA-based polymerization reaction. Blocking and deblocking of the Lysine NCA may be carried out similarly as in Examples 6-8.

According to embodiments of the present invention, any combination of one or more types of NCA-containing monomer(s), including NCA-amino acid(s) and/or NCA-compound(s), may potentially be used in an NCA-based polymerization reaction according to embodiments of the present invention. As described above, the relative concentrations of different NCA-containing monomer(s) in an NCA-based polymerization reaction may be used to determine their approximate relative proportions in final polymer products of the reaction, including their relative proportions within individual polymer products. According to some embodiments, co-polymers of different NCA-amino acids may be used to create pockets having different chemical properties within the folded tertiary structure of the synthesized polymer. For example, a co-polymer of lysine and glutamic acid may create pockets within the folded polymer having divergent acidic or basic side chains, or alternatively, for example, a co-polymer of tyrosine and glutamic acid may create pockets within the folded polymer having divergent hydrophilic or hydrophobic side chains. Such hydrophilic/hydrophobic examples may orient the folding of the polymer such that the hydrophobic monomers tend to be oriented toward the interior of the folded polymer and the hydrophilic monomers tend to be oriented toward the surrounding aqueous environment. Such co-polymers may be used, for example, in formulating certain pharmaceutical compounds, such as by containing an active agent or drug (especially a hydrophobic agent or drug) within the interior of the folded co-polymer.

In terms of their concentrations, the ratio of initiator(s) to NCA-containing monomer(s) may also be important. According to some embodiments of the present invention, the ratio of initiator(s) to NCA-containing monomer(s) (I/M ratio) may be used to determine or approximate the average length of polymer products, such as polypeptides, peptide-linked compounds, etc., synthesized by an NCA-based polymerization reaction. Assuming that the reaction proceeds at least near to completion, the distribution of molecular weights and polymer lengths of polymer products, such as polypeptides, peptide-linked compounds, etc., synthesized by an NCA-based polymerization reaction may approximate the I/M ratio of concentrations. For example, if the ratio of initiator(s) to NCA-containing monomer(s) is about 1:25, then the average length and size of polymer products of the polymerization reaction may be about twenty-five monomers and one initiator with the initiator covalently attached to the carboxyl end of the polymer product. Alternatively, for example, if the I/M ratio is about 1:1, then the average length of polymer products synthesized by the polymerization reaction may be a dimer of one initiator and one monomer bound together.

According to some embodiments of the present invention, the ranges of molecular weights, polymer lengths, etc., may vary widely to suit a particular application. For example, polymer products, such as polypeptides, peptide-linked compounds, etc., of an NCA-based polymerization reaction may be designed to have an average length to achieve a desired rate of sustained drug delivery. If the polymer product of the reaction is defined as $I\text{-}(M)_n$, with I=initiator (or sum of initiators), M=monomer (or sum of monomers), and n=number of total monomer units, then the n value may be, for example, anywhere from 1 to 1000 or higher. For example, the n value may be any value from about 1 to about 100, or alternatively, any value from about 1 to about 10. However, even though the average polymer size synthesized by present methods may approximate the I/M ratio present in the polymerization reaction, the exact distribution of molecular weight sizes and lengths of polymer products, such as polypeptides, peptide-linked compounds, etc., of a polymerization reaction may be somewhat heterogeneous and have a Poisson distribution that depends on reaction conditions. Such heterogeneous distribution of polymer sizes may have the benefit of broadening the time release profile of an orally administered drug since smaller fragments may generally digest and release the drug more quickly than larger fragments.

With these principles in mind, embodiments of the present invention may be designed to synthesize polymers, such as polypeptides, peptide-linked compounds, etc., to suit particular applications. Different polymer products may be synthesized by a single NCA-based polymerization reaction, in part because the process is largely stochastic (i.e., random) and driven by the relative proportions or concentrations of each of the reaction components including one or more different types of initiator(s) and/or monomer(s). When a mixture of different initiator(s) and/or NCA-containing monomer(s) are used in a NCA-based polymerization reaction, individual products of the reaction may comprise different ratios, proportions, types, order, etc., of the initiator(s) and/or monomer(s). However, the average proportions of monomer(s) and initiator(s) in polymer products of the polymerization reaction may roughly correspond to the relative concentrations of NCA-containing monomer(s) and initiator(s) in the reaction mixture. According to some embodiments, one or more active agent(s), compound(s), and/or drug(s) may be incorporated into a single polymer, such as a polypeptide, a peptide-linked compound, etc., as either initiator(s) or monomer(s), or both. Furthermore, different active agent(s), compound(s), and/or drug(s) may be incorporated into the same polymer products to allow for their combined use. Alternatively, a homopolymer may be formed.

Although some embodiments described herein refer to pharmaceutical applications, polymer products synthesized by embodiments of the present invention may also be applied to a diversity of other industrial or agricultural products and applications where NCA-based methods may be used. For example, as mentioned above, a glutamine-initiated polymer containing a tail of glutamic acids may be used in cell culture growth mediums.

EXAMPLES

It should be appreciated that all examples in the present disclosure, while illustrating many embodiments of the invention, are provided as non-limiting examples and are, therefore, not to be taken as limiting the various aspects so illustrated.

Example 1

Synthesis of Glutamic Acid N-Carboxyanhydride (Glu-NCA)

The following is an exemplary procedure for making an N-carboxyanhydride (NCA) glutamic acid (Glu-NCA) for use as an NCA-containing monomer. To a clean, dry 2 liter round bottom flask with a stirrer, triphosgene (e.g., about 54 gm±0.1 gm, 182 mmol) and purified glutamic acid (e.g., about 36.8 gm±0.1 or about 250 mmol) may be added, followed by the addition of anhydrous (e.g., about 0.002% water or less by Karl Fisher test) tetrahydrofuran (e.g., about 1.00 liter±0.01). This reaction may be warmed and maintained under gentle reflux in a bath at about 60° C. (±2°) for about 4 hrs.±0.5 or until the reaction becomes homogeneous. The reaction may then be flash evaporated under reduced or vacuum pressure (e.g., a pressure reduced by about 29-30" of Hg relative to the surrounding environment) in a water bath at about 35° C. (±5°) until the residue turns solid and no more solvent condensate is formed.

The crude Glu-NCA product of the reaction may then be purified further by dissolution in about 100 ml of anhydrous THF at about 55° C. (±5°). Any undissolved glutamic acid may then be filtered off, and about 100 ml of anhydrous ethyl acetate (e.g., about 0.005% or less water by Karl fisher test) may then be added and followed by the rapid addition of anhydrous hexane. The solution may then be cooled to about 4° C.±2° for full precipitation. The precipitate may then be filtered, washed with about 100 ml of anhydrous hexane, and compressed with a rubber dam to remove solvent and restrict exposure to air and moisture. For final purification, the hexane-wet filter "cake" may be dissolved in about 120 ml±5 ml of dry THF, insoluble precipitate may then be filtered off, and the purified Glu-NCA product may be purified further by rapid addition of 120 ml±5 ml of dry hexane. The Glu-NCA may then be cooled for full precipitation at about 4° C.±2°, filtered, and washed with hexane under dry under oil vacuum at about 20° C.±2°. In one experiment, a yield of about 30 gm (~69% yield) of purified Glu-NCA as a white, crystalline powder was observed. Such Glu-NCA is suitable for use in a subsequent polymerization reaction as in Example 2.

Example 2

Synthesis of Polymeric Glutamic Acid (PGlu)

The following is an exemplary procedure for making a glutamic acid homopolymer using glutamic acid as an initiator and glutamic acid-NCA as an NCA-containing monomer with an I/M ratio of about 1:25 according to some embodiments of the present invention, although other ratios may also be similarly used. Purified NCA-glutamic acid (17.3 gm, 100 mmol), such as the NCA-glutamic acid from Example 1, may be combined with purified glutamic acid (e.g., about 0.59 gm or about 4 mmol in free acid form) along with about 50.0 ml anhydrous THF and about 50.0 ml of anhydrous dioxane in a 250 ml round bottom flask. Such reaction may then be placed under reduced pressure or vacuum in a temperature controlled bath. The bath temperature may be raised to about 65° C. with evolution of $CO_2$ as the reaction proceeds. The reaction may first become homogeneous before converting to a solid polymer after about 15 min. However, the reaction may be maintained under vacuum at about 65° C. for an additional 10 min and then cooled on ice. The glutamic acid polypeptide product of the polymerization may then be purified by extraction with about 25 ml of anhydrous THF, and a white precipitate may be isolated by filtration, washed with about 20 ml of THF, and dried at about 25° C.±5° in a vacuum oven. In one experiment, a yield of about 11.1 gm (~86%) of dry, white powder was observed.

Example 3

Synthesis of Glutamic Acid/Amphetamine Co-polymer (PGlu/A)

As an example of a procedure used to synthesize a polymer composed of an active agent compound used an initiator for polymerization of a glutamic acid tail—i.e. Amphetamine-$(Glu)_n$. In general, the procedure may be the same as described in Example 2, except that D-Amphetamine (free amine) is used instead of glutamic acid as an initiator for polymerization with Glu-NCA. For example, about 1.35 gm or about 10 mmol of D-Amphetamine may be used to initiate polymerization of with about 17.3 gm or about 100 mmol Glu-NCA monomer. The D-Amphetamine/glutamic acid polymer (PolyGlu-Amp) product may be further purified by extraction with about 20 ml of anhydrous THF to form a white precipitate that may be isolated by filtration, washed with about 10 ml THF, and dried in a vacuum oven at about 25° C.±5°. Such protocol was used to yield about 13.8 gm of dry white powder, which may be suitable for formulation into tablets, etc.

Example 4

Formulation and Tableting of PolyGlu-Amp

The following table provides an exemplary formulation recipe for a tablet containing PolyGlu-Amp (e.g., from Example 3) and PolyGlu (e.g., from Example 2) as an excipient:

TABLE 1

| Formulation Recipe. | | |
|---|---|---|
| Component | Source | Mass/Tablet (mg) |
| 1. Microcrystalline Cellulose 102 | FMC | 100 |
| 2. PolyGlu | ITL | 100/50 |
| 3. PolyGlu-Amp (10, 20 mg) | ITL | 50/100 |
| 4. Cross Carmelose | FMC | 2.0 |
| 5. Magnesium Stearate | Merck | 2.0 |
| | | Total: 254 mg ± 5 mg |

Microcrystalline cellulose, Poly-Glu (e.g., from Example 2), and PolyGlu-Amp (e.g., from Example 3) may be combined and blended by rotation in a cone blender for about 12.5 min at about 1 rev/5 sec (i.e., about 150×360° rotations). The amount of PolyGlu-Amp may be adjusted for dosage (e.g., 10 or 20 mg may be required by a clinical protocol). However, the sum of PolyGlu and PolyGlu-Amp together may be about 150 mg. Mg stearate may be added to the mixture and blended again for about 7.5 min. at about 1 rev/sec (i.e., about 90 rotations). About 254 mg±5 mg tablets may then be prepared by direct compression to a hardness of about 12-14 KPa. Granulation may not be required.

Example 5

Pharmacokinetics of PolyGlu-Amphetamine

Tablets prepared according to the formulation in Example 4 may be used in a chemical assessment of time-release and pharmacokinetic properties of PolyGlu-Amp availability on the basis of its half-life in the blood. For these studies, Poly-Glu-Amp may be synthesized using D-Amphetamine with its 6 aromatic ring carbons labeled with the stable $^{13}C$ isotope. Blood samples may then be taken over a period of time after oral administration of tablets containing PolyGlu-Amp and analyzed using a HPLC Tandem Mass spectrometer system. In these experiments, it was observed that orally administered PolyGlu-Amp had extended release properties compared to non-polymerized D-amphetamine.

Example 6

Synthesis of CBZ-Lysine N-Carboxyanhydride (CBZ-Lys-NCA)

Certain amino acids contain reactive functional groups on the side chain that require blocking to allow efficient NCA and polymerization chemistry. In this example, N(epsilon)-CBZ-L-Lysine is converted to the corresponding N-carboxyanhydride (NCA) for further use in an NCA-based polymerization reaction. To a clean, dry 2 liter round bottom flask, fitted with a mechanical stirrer, anhydrous (e.g., about 0.002% water or less by Karl Fisher test) tetrahydrofuran, triphosgene (24.5 gm±0.1 gm, 250 mEq) and CBZ-lysine (35.0 gm±0.1 gm) are added and mixed to form a uniform suspension. The reaction is allowed to proceed, such as for about 4 hr±10 min, under gentle reflux with an open end condenser fitted with a drying tube. The reaction is evaporated in an about 40° C.±5° C. water bath to dryness without further accumulation of condensate. The dry precipitate is dissolved in dry (e.g., about 0.002% water or less by Karl Fisher test) ethyl acetate in a 50° C. water bath. Any undissolved haze is filtered out, and the crude NCA product is precipitated by the rapid addition of hexane. The mixture is cooled on ice for about 20 minutes to fully precipitate, and the product is isolated by filtration. The filter cake is washed with about 200 ml of hexane and compressed with a rubber dam. The compressed product is then washed with approximately another 200 ml of hexane. The product is dried in vacuo at about 50° C. to obtain about 32 gm (i.e., 78% yield). A second crop of about 2 grams may be obtained from the refrigerated filtrate. This dried product is suitable for polymer formation in an NCA-based polymerization reaction without further purification.

Example 7

Synthesis of 3,5,3'-Triiodo-L-Thyronine initiated, CBZ-Lysine polymer (PolyCBZLys/T3)

In this example, a poly-Lysine polymer is synthesized in an NCA-based polymerization reaction to contain the active agent, 3,5,3'-Triiodo-L-Thyronine (T3), used as an initiator. In a 200 ml round bottom flask, 50 ml anhydrous tetrahydrofuran, 50 ml of anhydrous dioxane, 15.31 gm (about 50 mmol) CBZ-Lys-NCA (e.g., the product of Example 6), 0.326 gm (about 0.5 mmol) 3,5,3'-Triiodo-L-Thyronine (T3, free acid) are combined and mixed until dissolved. Using continuous mixing under vacuum, the reaction temperature is ramped from about 50° C. to about 90° C. in a water bath for about 45 minutes. During this temperature ramp, the solvent is removed and $CO_2$ will evolve as the polymerization reaction proceeds. At the end of the reaction, a solid polymer product is formed with no additional evolution of $CO_2$. This product (about 14 gm) is suitable for deblocking as in Example 8.

Example 8

Deblocking of Poly-CBZ-Lys/T3 to form Poly-Lys/T3

The CBZ blocking groups on epsilon amino groups of lysine monomers in the polymer are removed using hydrobromic acid (HBr) in acetic acid. The Poly-CBZ-Lys/T3 polymer product of Example 7 is dissolved in about 50 ml of glacial acetic acid at about 85° C. in a 250 ml round bottom flask, to produce a clear solution of the polymer. The solution (about 42.0 ml) of 33% HBr in acetic acid is added to the reaction and is heated to about 80° C. for about 60 min in a hood. Evolution of $CO_2$ bubbles indicates deblocking. The deblocked polymer is minimally soluble in acetic acid and precipitates as the deblocking reaction proceeds. The supernatant is decanted from the polymer precipitate and 100 ml of acetic acid is added with mixing to wash the precipitate. The supernatant is decanted, and the precipitate is washed again with about 100 ml of acetic acid, which is then decanted. This is followed by 100 ml of acetone with good mixing. The polymer product is filtered, and the filter cake is washed with about 25 ml of acetone and dried in vacuo to obtain the product with about 87% yield. T3 content in the polymer may be determined using elemental analysis using Iodine as a reporter element. Pronase digestion of the polymer followed by high pressure liquid chromatography may be used to confirm the integrity of the T3-containing polymer.

While the present invention has been disclosed with references to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method comprising the following steps:
   (a) combining one or more initiators and one or more NCA-containing monomers in a reaction vessel to form a reaction mixture; and
   (b) heating the reaction mixture to an elevated temperature at or above the melting point of at least one of the NCA-containing monomers, wherein at least one of the NCA-containing monomers melts at the elevated temperature during step (b),
   wherein the elevated temperature is in a range from about 55° C. to about 70° C.

2. The method of claim 1, further comprising:
   (c) maintaining the temperature of the reaction mixture heated in step (b) at or above the melting point of the at least one NCA-containing monomer melted in step (b) until an NCA-based polymerization reaction involving the one or more initiators and the one or more NCA-containing monomers reaches or nears completion.

3. The method of claim 2, wherein the maintaining step (c) is carried out until evolution of $CO_2$ from the reaction mixture is no longer visible.

4. The method of claim 2, wherein the maintaining step (c) is carried out until a visible solid precipitate is formed in the reaction mixture.

5. The method of claim 1, wherein the one or more initiators comprises two or more different types of initiators.

6. The method of claim 1, wherein the one or more NCA-containing monomers comprises two or more different types of NCA-containing monomers.

7. A method comprising the following steps:
   (a) combining one or more initiators and one or more NCA-containing monomers in a reaction vessel to form a reaction mixture; and
   (b) heating the reaction mixture to an elevated temperature at or above the melting point of at least one of the NCA-containing monomers, wherein at least one of the NCA-containing monomers melts at the elevated temperature during step (b),
   wherein at least one of the one or more initiators is an active agent or drug,.
   wherein the active agent or drug is amphetamine, serotonin, catecholamine, L-DOPA, dopamine, 3,5,5',3'-tetraiodo-L-thyronine (T4), or 3,5,3'-triiodo-L-thyronine (T3).

8. The method of claim 7, wherein the one or more initiators and the one or more NCA-containing monomers are combined in step (a) in an aprotic solvent.

9. A method comprising the following steps:
   (a) combining one or more initiators and one or more NCA-containing monomers in an aprotic solvent in a reaction vessel to form a reaction mixture; and
   (b) heating the reaction mixture to an elevated temperature at or above the melting point of at least one of the NCA-containing monomers, wherein at least one of the NCA-containing monomers melts at the elevated temperature during step (b),
   wherein the elevated temperature is above the boiling point of the aprotic solvent.

10. The method of claim 9, wherein the base monomer of at least one of the one or more NCA-containing monomers is an active agent or drug.

11. The method of claim 10, wherein the active agent or drug is L-DOPA, 3,5,3',5'-tetraiodothyronine (T4), or 3,5,3'-triiodo-L-thyronine (T3).

12. The method of claim 9, wherein most or all of the aprotic solvent evaporates or boils out of the reaction mixture during step (b).

13. The method of claim 9, wherein the one or more initiators and the one or more NCA-containing monomers are homogeneously mixed in the aprotic solvent in step (a).

14. The method of claim 9, wherein the aprotic solvent has a boiling point below the melting point of the at least one NCA-containing monomer melted during step (b).

15. The method of claim 9, further comprising:
   (c) maintaining the temperature of the reaction mixture heated in step (b) at or above the melting point of the at least one NCA-containing monomer melted in step (b) until an NCA-based polymerization reaction involving the one or more initiators and the one or more NCA-containing monomers reaches or nears completion.

16. The method of claim 9, wherein at least one of the one or more initiators is an active agent or drug.

17. The method of claim 16, wherein the active agent or drug is amphetamine, serotonin, catecholamine, L-DOPA, dopamine, 3,5,5',3'-tetraiodo-L-thyronine (T4), or 3,5,3'triiodo-L-thyronine (T3).

18. The method of claim 17, wherein the active agent or drug is amphetamine.

19. The method of claim 9, wherein the ratio of the amount of the one or more initiators to the amount of the one or more NCA-containing monomers combined in step (a) is chosen to determine the average length of polymers produced by an NCA-based polymerization reaction involving the one or more initiators and the one or more NCA-containing monomers.

20. The method of claim 9, wherein the aprotic solvent comprises one or more of the following: perfluorohexane, pentane, hexane, cyclohexane, carbon tetrachloride, benzene, carbon disulfide, diisopropyl ether, diethyl ether, t-butyl methyl ether (MTBE), chloroform, ethyl acetate, tetrahydrofuran (THF), methylene chloride, 2-butanone, acetone, acetonitrile, dichloromethane, or nitrobenzene.

21. The method of claim 9, wherein the elevated temperature is in a range from about 50 to about 75° C.

22. The method of claim 9, further comprising:
   (c) applying a reduced pressure to the reaction mixture.

23. The method of claim 22, wherein the reduced pressure is between zero inches of Hg to about 20 inches of Hg.

24. The method of claim 22, wherein step (c) is performed during step (b).

25. The method of claim 22, wherein step (c) is performed after step (a).

* * * * *